(12) United States Patent
Abboud et al.

(10) Patent No.: US 8,361,059 B2
(45) Date of Patent: Jan. 29, 2013

(54) COOLING SYSTEM

(75) Inventors: Marwan Abboud, Pierrefonds (CA); Rachid Mahrouche, Anjou (CA); Jean-Pierre Lalonde, Verdun (CA); Dan Wittenberger, Pierrefonds (CA)

(73) Assignee: Medtronic Cryocath LP, Toronto, Ontario ( * ) Notice: Subject to any disclaimer, the term of this patent is extended or adjusted under 35 U.S.C. 154(b) by 1051 days.

(21) Appl. No.: 11/581,185

(22) Filed: Oct. 13, 2006

(65) Prior Publication Data

US 2007/0093799 A1 Apr. 26, 2007

Related U.S. Application Data

(63) Continuation of application No. 10/619,366, filed on Jul. 14, 2003, now Pat. No. 7,207,986, which is a continuation of application No. 09/771,031, filed on Jan. 26, 2001, now Pat. No. 6,592,577, which is a continuation-in-part of application No. 09/638,208, (Continued)

(51) Int. Cl.
*A61B 18/02* (2006.01)
(52) U.S. Cl. ............................................. 606/22
(58) Field of Classification Search ............... 606/20–26; 607/104–105
See application file for complete search history.

(56) References Cited

U.S. PATENT DOCUMENTS

| | | | |
|---|---|---|---|
| 3,823,575 A | 7/1974 | Parel | |
| 3,859,986 A | 1/1975 | Okada et al. | |
| 5,275,595 A * | 1/1994 | Dobak, III | 606/23 |
| 5,334,181 A * | 8/1994 | Rubinsky et al. | 606/22 |
| 5,651,780 A | 7/1997 | Jackson et al. | |
| 5,658,278 A | 8/1997 | Imran et al. | |
| 5,674,218 A | 10/1997 | Rubinsky et al. | |
| 5,743,903 A | 4/1998 | Stern et al. | |
| 5,758,505 A | 6/1998 | Dobak, III et al. | |
| 5,807,391 A * | 9/1998 | Wijkamp | 606/23 |
| 5,957,963 A | 9/1999 | Dobak, III | |
| 6,007,571 A | 12/1999 | Neilson et al. | |
| 6,016,661 A | 1/2000 | Sagar | |
| 6,019,783 A | 2/2000 | Philips et al. | |
| 6,027,499 A | 2/2000 | Johnston et al. | |
| 6,027,500 A | 2/2000 | Buckles et al. | |
| 6,032,675 A | 3/2000 | Rubinsky | |
| 6,033,383 A | 3/2000 | Ginsburg | |
| 6,039,730 A | 3/2000 | Rabin et al. | |
| 6,051,019 A | 4/2000 | Dobak, III | |
| 6,096,068 A | 8/2000 | Dobak, III et al. | |
| 6,106,518 A | 8/2000 | Wittenberger et al. | |
| 6,146,411 A | 11/2000 | Noda et al. | |
| 6,149,677 A | 11/2000 | Dobak, III | |

(Continued)

FOREIGN PATENT DOCUMENTS

| | | |
|---|---|---|
| EP | 0651308 A1 | 3/1995 |
| GB | 2026324 A | 2/1980 |

(Continued)

*Primary Examiner* — Michael Peffley
*Assistant Examiner* — Ronald Hupczey, Jr.
(74) *Attorney, Agent, or Firm* — Christopher & Weisberg, P.A.

(57) ABSTRACT

A cryogenic medical system includes a medical device and a console connectable to the medical device at a connection point. The console controls the temperature of the medical device. The console includes a first cooling system directing coolant to the medical device at a first temperature along a coolant supply line and a second cooling system chilling the coolant within the coolant supply line to a temperature below the first temperature before the coolant reaches the connection point.

12 Claims, 12 Drawing Sheets

Related U.S. Application Data filed on Aug. 11, 2000, now Pat. No. 6,635,053, which is a continuation-in-part of application No. 09/489,646, filed on Jan. 24, 2000, now Pat. No. 6,383,180.

(60) Provisional application No. 60/117,175, filed on Jan. 25, 1999.

(56) References Cited

U.S. PATENT DOCUMENTS

| | | |
|---|---|---|
| 6,161,543 A | 12/2000 | Cox et al. |
| 6,190,378 B1 | 2/2001 | Jarvinen |
| 6,193,644 B1 | 2/2001 | Dobak, III et al. |
| 6,235,048 B1 | 5/2001 | Dobak, III |
| 6,241,722 B1 | 6/2001 | Dobak et al. |
| 6,306,129 B1 | 10/2001 | Little et al. |
| 6,468,268 B1 | 10/2002 | Abboud et al. |
| 6,471,694 B1 | 10/2002 | Kudaravalli et al. |
| 2007/0093799 A1 | 4/2007 | Abboud et al. |

FOREIGN PATENT DOCUMENTS

| | | |
|---|---|---|
| WO | 9630816 A1 | 10/1996 |
| WO | 9837822 A1 | 9/1998 |
| WO | 9956639 A1 | 11/1999 |
| WO | 9956640 A1 | 11/1999 |
| WO | 9956641 A1 | 11/1999 |
| WO | 9957494 A1 | 11/1999 |
| WO | 0035362 A2 | 6/2000 |
| WO | 0101049 A1 | 1/2001 |

* cited by examiner

COOLING SYSTEM

CROSS-REFERENCE TO RELATED APPLICATIONS

This application is a Continuation of application Ser. No. 10/619,366, filed Jul. 14, 2003, by Marwan Abboud, et al., entitled COOLING SYSTEM, now U.S. Pat. No. 7,207,986, issued Apr. 24, 2007, which is a Continuation of U.S. patent application Ser. No. 09/771,031, filed Jan. 26, 2001, by Marwan Abboud, et al., entitled COOLING SYSTEM, now issued U.S. Pat. No. 6,592,577, issued Jul. 15, 2003, which application is a Continuation-in-Part of U.S. patent application Ser. No. 09/638,208 filed Aug. 11, 2000, by Marwan Abboud, et al., entitled COOLING SYSTEM, now issued U.S. Pat. No. 6,635,053, issued Oct. 21, 2003, which application is a Continuation-in-Part of U.S. patent application Ser. No. 09/489,646, filed Jan. 24, 2000, by Jean-Pierre Lalonde, et al entitled CLOSED LOOP CATHETER SYSTEM, now issued U.S. Pat. No. 6,383,180, issued May 7, 2002, which application claims priority from U.S. Provisional Patent Application No. 60/117,175, filed Jan. 25, 1999, by Marwan Abboud, et al., entitled CRYOABLATION SYSTEM, now expired, the entirety of all of which are incorporated herein by reference.

STATEMENT REGARDING FEDERALLY SPONSORED RESEARCH

Not Applicable.

FIELD OF THE INVENTION

The present invention relates to a coolant system for a catheter or treatment wand used for cryotreatment of tissue. In particular, the coolant system is of the type which connects to a catheter and pumps coolant through the catheter to chill a region of the catheter, such as the distal tip, for treating tissue.

BACKGROUND OF THE INVENTION

A number of cooled catheter systems have been developed for treating tissue in a cardiac setting, either to cool the tissue sufficiently to stun it and allow cold mapping of the heart and/or confirmation of catheter position with respect to localized tissue lesions, or to apply a more severe level of cold to ablate tissue at the site of the catheter ending. In general, the range of treatments which may be effected by a cryocatheter is comparable to the range of applications for radio frequency or thermal ablation catheters, and in particular, these instruments may be configured to achieve either small localized ball shape lesions at the tip of the catheter, or one or more elongated linear lesions extending a length of several centimeters or more along the tip. The latter form of lesion is commonly used to achieve conduction block across a region of the cardiac wall so as to sever an aberrant pathway over a length, preventing conduction across the region, in order change the cardiac signal path topology, for example, to eliminate a faulty pathway responsible for atrial fibrillation or a tachycardia.

In general, when used for endovascular access to treat the cardiac wall, catheters of this type, in common with the corresponding earlier-developed radio frequency or electrothermal ablation catheter, must meet fairly demanding limitations regarding their size, flexibility, and the factors of strength, electrical conductivity and the like which affect their safety and may give rise to failure modes in use. These constraints generally require that the catheter be no larger than several millimeters in diameter so as to pass through the vascular system of the patient to the heart. Thus, any electrodes (in the case of mapping or RF/electrothermal ablation catheters), and any coolant passages (in the case of cryocatheters) must fit within a catheter body of small size.

A number of different fluids have been used for the coolant component of prior art cryotreatment catheters, such as a concentrated saline solution or other liquid of suitably low freezing point and viscosity, and of suitably high thermal conductivity and heat capacity, or a liquified gas such as liquid nitrogen. In all such constructions, the coolant must circulate through the catheter, thus necessitating multiple passages leading to the cooling area of the tip from the catheter handle.

Furthermore, conditions of patient safety must be considered, raising numerous problems or design constraints for each particular system. Thus for example, a high pressure may be required to circulate sufficient coolant through the catheter body to its tip and back, and the overall design of a catheter must be such that fracture of the catheter wall or leakage of the coolant either does not occur, or if it occurs, is harmless. Further, for an endovascular catheter construction, the presence of the coolant and circulation system should not substantially impair the flexibility or maneuverability of the catheter tip and body.

To some extent these considerations have been addressed by using a phase change material as the cryogenic fluid, and arranging the catheter such that the phase change, e.g., from a liquid to a gas, occurs in the treatment portion of the catheter tip. Another possible approach is to employ a pressurized gas, and configure the catheter for cooling by expansion of the gas in the tip structure. However, owing to the small size that such a catheter is required to assume for vascular insertion, or the awkwardness of handling a cryogenic treatment probe generally, the design of a safe and effective coolant circulation system which nonetheless dependably provides sufficient cooling capacity at a remote tip remains a difficult goal.

Among other common problems to be addressed while providing adequate thermal capacity, may be noted the leakage problem mentioned above, the problem of effectively preventing the catheter as a whole from being excessively cold or damaging tissue away from the intended site, and the problem of conduit or valve blockage owing for example to ice particles and the like.

Accordingly, it would be desirable to provide a coolant system which conveniently attaches to a cryocatheter.

It would also be desirable to provide a coolant system which injects and retrieves the coolant from the catheter to allow continuous operation without leakage into the environment or other loss of coolant.

It would further be desirable to provide a treatment system which precisely controls ablation and treatment regimens by conditioning the coolant supply at various point along the fluid path.

SUMMARY OF THE INVENTION

These and other desirable features are obtained in a coolant system that includes a medical device and a console connectable to the medical device at a connection point. The console controls the temperature of the medical device. The console includes a first cooling system directing coolant to the medical device at a first temperature along a coolant supply line and a second cooling system chilling the coolant within the coolant supply line to a temperature below the first temperature before the coolant reaches the connection point.

BRIEF DESCRIPTION OF DRAWINGS

These and other features of the invention will be understood by reference to the description below, read in light of the prior art together with illustrative figures, wherein.

DETAILED DESCRIPTION OF INVENTION

Figure 1:
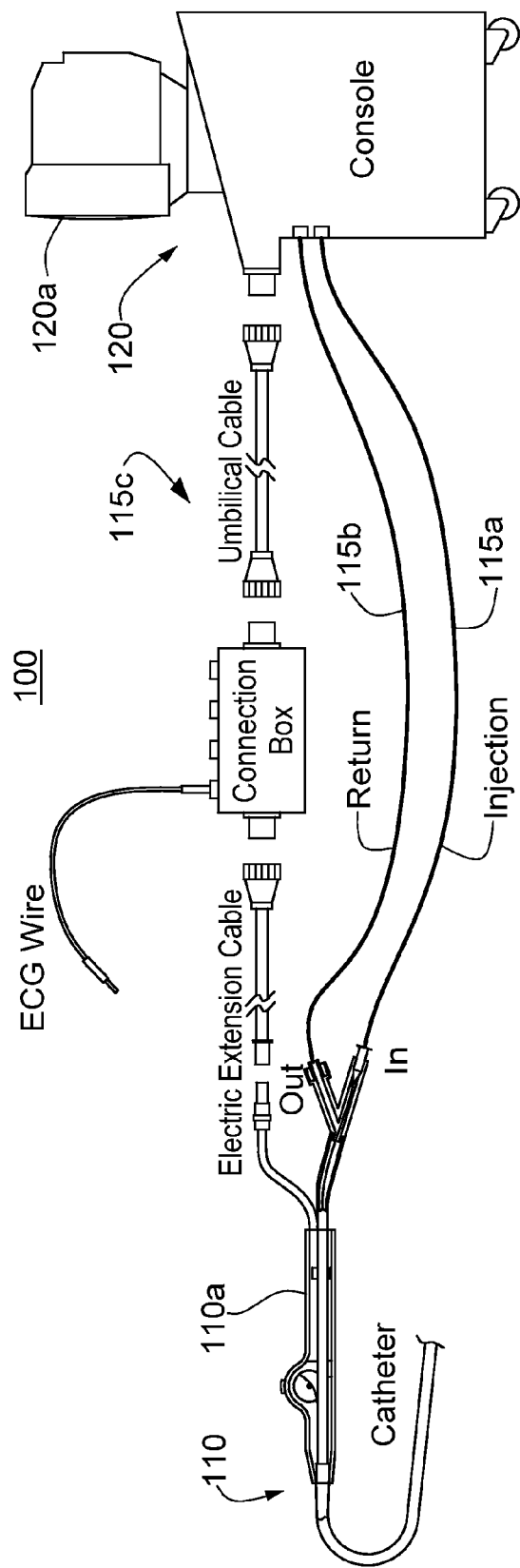
FIGS. 1 and 1A illustrate a cryocatheter treatment system and cryocatheter.

FIG. 1 shows a cryogenic treatment system 100 illustrating the general elements thereof. System 100 includes a treatment catheter 110 having a handle 110a, a treatment console 120 and number of connecting lines 115 which include signal lines for any monitoring or mapping functions as well as a coolant injection line 115a and a coolant return line 115b. As illustrated, the console includes a display screen 120a which may, for example, show both cardiac electrical signals and various status and control screens related to setting or reporting the cooling functions of the catheter or the ablation regimens being administered therewith.

Figure 1A:
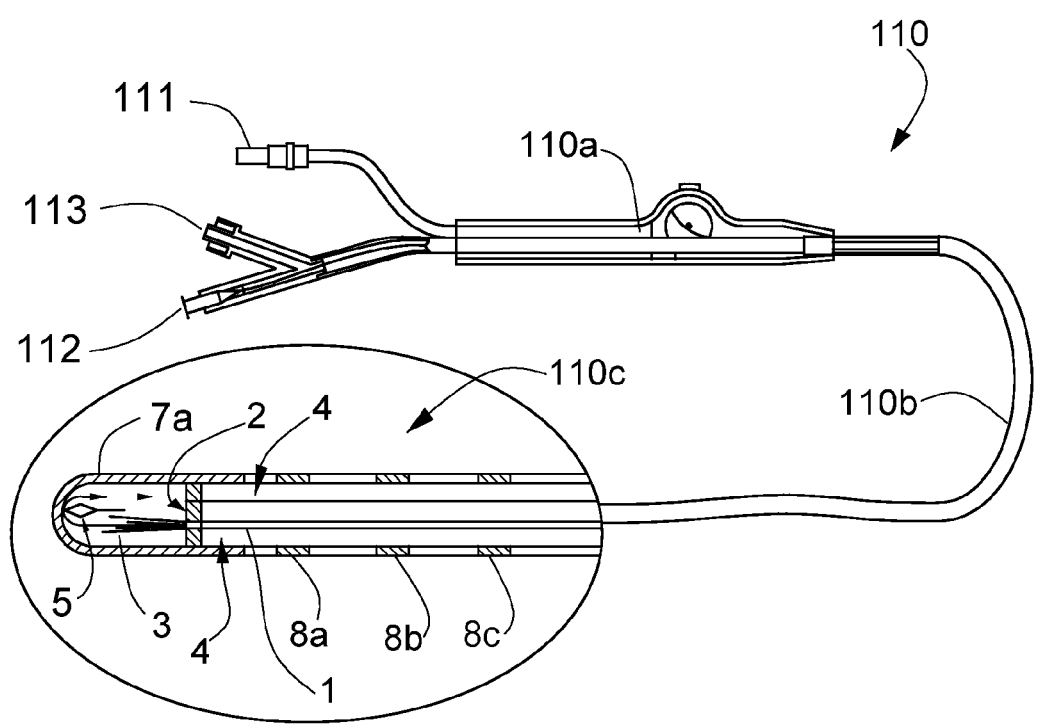

FIG. 1A shows in slightly greater detail a catheter 110 used in a system in accordance with the present invention. As shown, the handle 110a is equipped with input ports for an electrical connector 111, a coolant injection tube connector 112, and a return tube connector 113. These connect via various internal junctions or tubes passing through the handle to provide these three functions to the distal tip of the catheter. The handle may also include various control assemblies, e.g., switches or valves, as well as safety detection or shut down elements (not illustrated).

Leading from the handle 110a is an elongated catheter body 110b which extends to the catheter tip 110c, illustrated in enlarged detail to show a representative structure thereof. As shown, in catheter tip 110c the coolant enters through a central tube 1 and exits via a nozzle 2 at the end of the tube to expand in a small contained region forming a chamber 3 at the tip of the catheter. In the illustrated construction, the tube 1 runs concentrically within an outer tube (not numbered) thereby forming an annular return space 4 surrounding the supply tube 1 and extending back to the fluid return connector 113 of the handle. As discussed further below, the return passage for expended coolant is a vacuum passage, thus assuring that leakage into the blood stream cannot occur.

The location of chamber 3 defines the cooling region of the catheter tip. In the illustrated embodiment this is a short chamber less than a centimeter long located at the very tip of the catheter. Also shown are a thermocouple 5 positioned within the tip to sense tip temperature, and a plurality of electrodes including a tip electrode 7a and one or more ring electrodes 8a, 8b . . . which are positioned near the tip for use in mapping and/or detecting cardiac signals. In other embodiments, the chamber 3 defined at the tip of the catheter may be an elongated chamber several centimeters in length for defining a coolant chamber effective to form linear lesions when placed in contact with tissue such as the cardiac wall. For the linear embodiment, multiple expansion nozzles, a perforated inlet tube end segment, or other variation in the construction of the coolant supply line may be used to assure a high rate of cooling along the full length of the expansion chamber. Furthermore, the chamber wall may be very thin, or formed with a metal sleeve or cap to achieve high heat transfer rates. Other structures within the catheter may include torque or steering wires, or other elements conventional in the art for navigation of the catheter past branch points in vessels, and for urging the catheter tip into contact with a wall once its position is confirmed.

As will be understood from the above, the task of the console is to provide coolant at the tip region in sufficient quantity and for times effective to create the desired lesions. The nature and depth of the lesions created will depend on a number of factors, including the temperature attained in the adjacent tissue, as well as the nature of the cooling cycle by which that temperature is attained. In general when the tissue attains an extremely low temperature, or a temperature effective to create ice crystals within tissue cells, the tissue damage will be irreversible, resulting in effective ablation at the contacted site. The actual cooling rates achieved at the tip will depend to a large extent on the area of contact with the tissue as well as the conductive properties of the adjacent tissue and the structure and geometry of the catheter in addition to the nature of coolant flow passing through the catheter tip. In the present system the latter quantity is controlled, as discussed more fully below, by providing a controller in which the flow of a phase change coolant supplied to the tip is varied to directly control the amount of cooling power available during an ablation cycle. In addition, the primary cooling effect is achieved by expansion of coolant at the inlet nozzle 2 as it enters chamber 3.

While not illustrated, one or more electrical sensing elements in addition to the thermocouple may be provided at various places within the catheter to provide useful feedback or emergency control functions. For purposes of the present patent application, such functions will not be further discussed. However, if provided they may be positioned in a discrete cooling system, which for purposes of illustration may be considered to lie entirely within the console 120, or be external thereto, but in any case to function in relation to the coolant supply elements which will now be described below.

Figure 2:
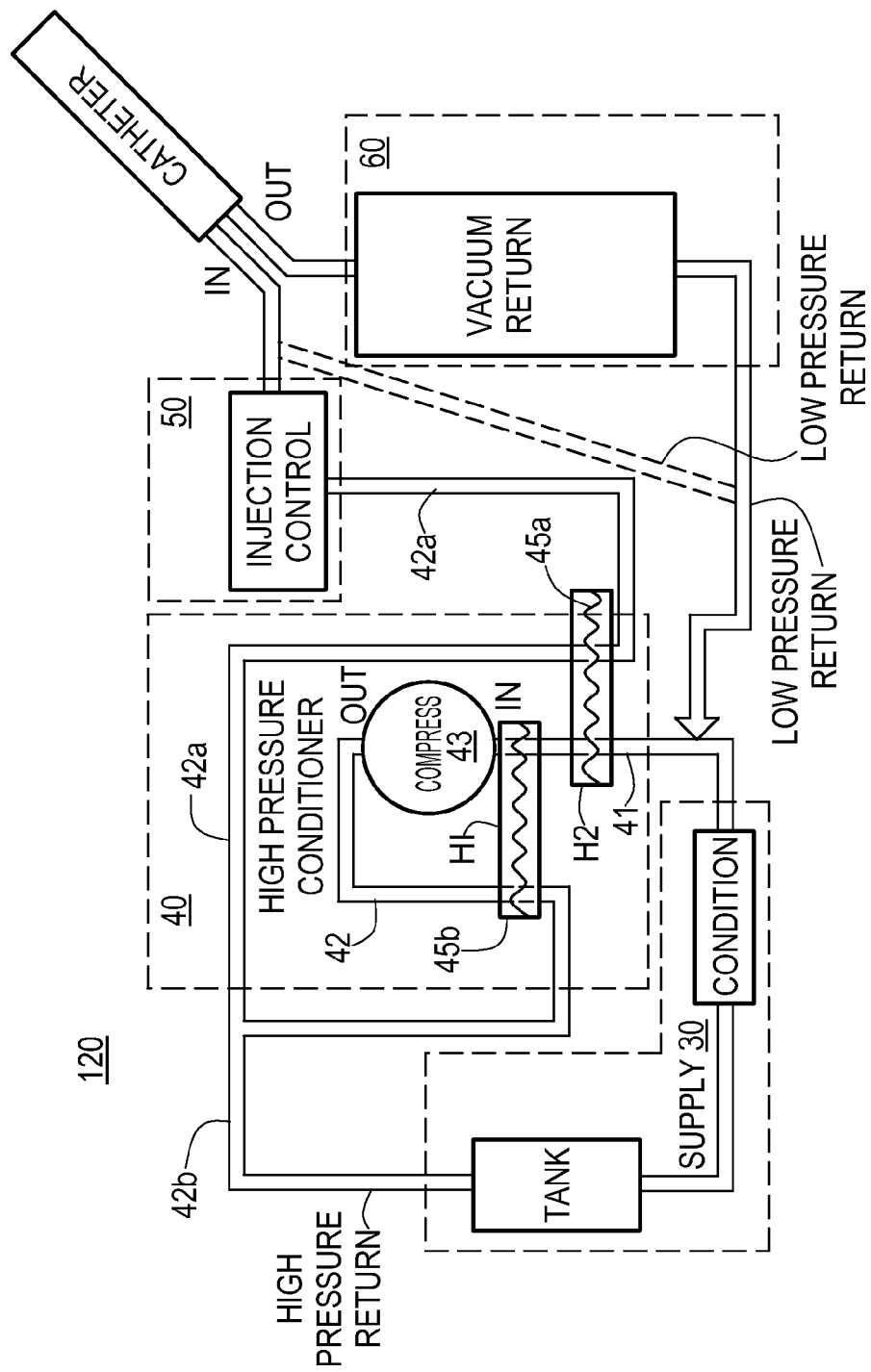
FIG. 2 is a schematic representation of a coolant system in accordance with one embodiment of the present invention for use with the catheter of FIG. 1.

FIG. 2 illustrates one embodiment of a cooling system in accordance with the present invention configured to connect to the inlet and return ports 112, 113 of the catheter 110 (FIG. 1A). As shown, the coolant system 120 includes a coolant supply 30, a coolant conditioner 40, a coolant control 50 and a coolant return section 60. The control section 50 connects to the inlet 112 of the injection catheter, for example by a supply tube, while the return system 60 connects to coolant return port 113. These are illustrated as separate connections, but as discussed more fully below, they may be implemented with a single vacuum-jacketed line with a quick connect coupler, or other specialized connection which allows a single coupling to the catheter handle for all coolant functions. Similarly, electrical connections may be incorporated in such a single conduit, or may be provided as separate signal cabling. Operation of the coolant system 120 will be most fully understood from a detailed discussion of each of the subassemblies 30, 40, 50, 60.

In general terms, the coolant system has a coolant conditioning section 40 with a compressor that provides a conditioned phase change coolant at elevated pressure to the control section 50, which, in turn, regulates the supply of coolant provided to the inlet of the catheter. The return section 60 includes a vacuum pump which continuously draws expended coolant from the catheter at lower pressure and returns it at higher pressure to the coolant conditioner 40, thereby providing a closed circulation loop through the catheter to meet the required ablation or mapping regimens. In the preferred embodiment, the conditioner provides coolant substantially at ambient temperature or colder, and the controller includes an electronically controlled pressure regulator which sets the flow rate of the coolant injected into the catheter, thus regulating the cooling action of the catheter tip. Conditioned coolant is provided to the control section by the conditioner 40, which receives coolant at lower pressure either from the return section 60 or from the supply 30, compresses the coolant to a high pressure, liquefies the coolant, and brings it to approximately ambient temperature at its outlet line 42a leading to the controller. As further shown in FIG. 2, the output from the compressor has a second branch 42b in which excess coolant is not further cooled, but is simply returned to the supply 30.

As noted above, conditioner section 40 in addition to the raising the pressure of the coolant supplied to the regulator for controlled injection into the catheter, also conditions the temperature of the high pressure coolant. This is preferably done as shown in FIG. 2, by heat exchange between the inlet supply line 41 and the compressor outlet line 42. As shown in the figure, the compressor outlet line 42 is placed in heat exchange communication, for example via a condenser or heat exchanger 45b, with the inlet line 41. In addition one output branch 42a of the outlet line 42 is placed in heat exchange communication, for example via exchanger 45a, with an upstream portion of the inlet line 41. The compressor 43 operates to compress the coolant from a relatively low pressure, preferably below atmospheric, to a considerably higher pressure, e.g., 20 to 30 atmospheres as measured in its outlet line 42. The material in line 42 is therefore heated by compression, and the heat exchange with inlet line 41 serves to reduce the temperature rise generated by compression. Furthermore, by providing only a portion of compressor output, namely the catheter-directed branch 42a to the upstream, colder portion of the compressor inlet line 41, the catheter injection supply of coolant is effectively brought to or near ambient temperature or colder, while the downstream heat exchange effected in heat exchanger 45b with the entire output of the compressor is cooled to a lesser extent, serving a more traditional function of liquefying the coolant output and enhancing the overall cooling capacity of the compressed fluid. This ordered heat exchange arrangement provides preferentially greater cooling to the catheter-directed supply line, resulting in a stabilized catheter input over a broader range of operating cycles.

In FIG. 2 the high pressure return 42b to the tank may be implemented with a pressure regulator located in-line ahead of the tank inlet to assure that coolant is returned to the tank only when its use elsewhere in the circulation loop is not required, and that the pressure in the line first builds up to a level higher than the current tank pressure.

Thus, the system of the present invention provides a closed-loop coolant circulation system wherein coolant is conditioned for provision to the inlet of a control module which injects the coolant into a catheter, and the coolant returns in a closed-loop to provide a continuous circulation of fluid at ambient temperature or colder into the catheter.

Figure 3:
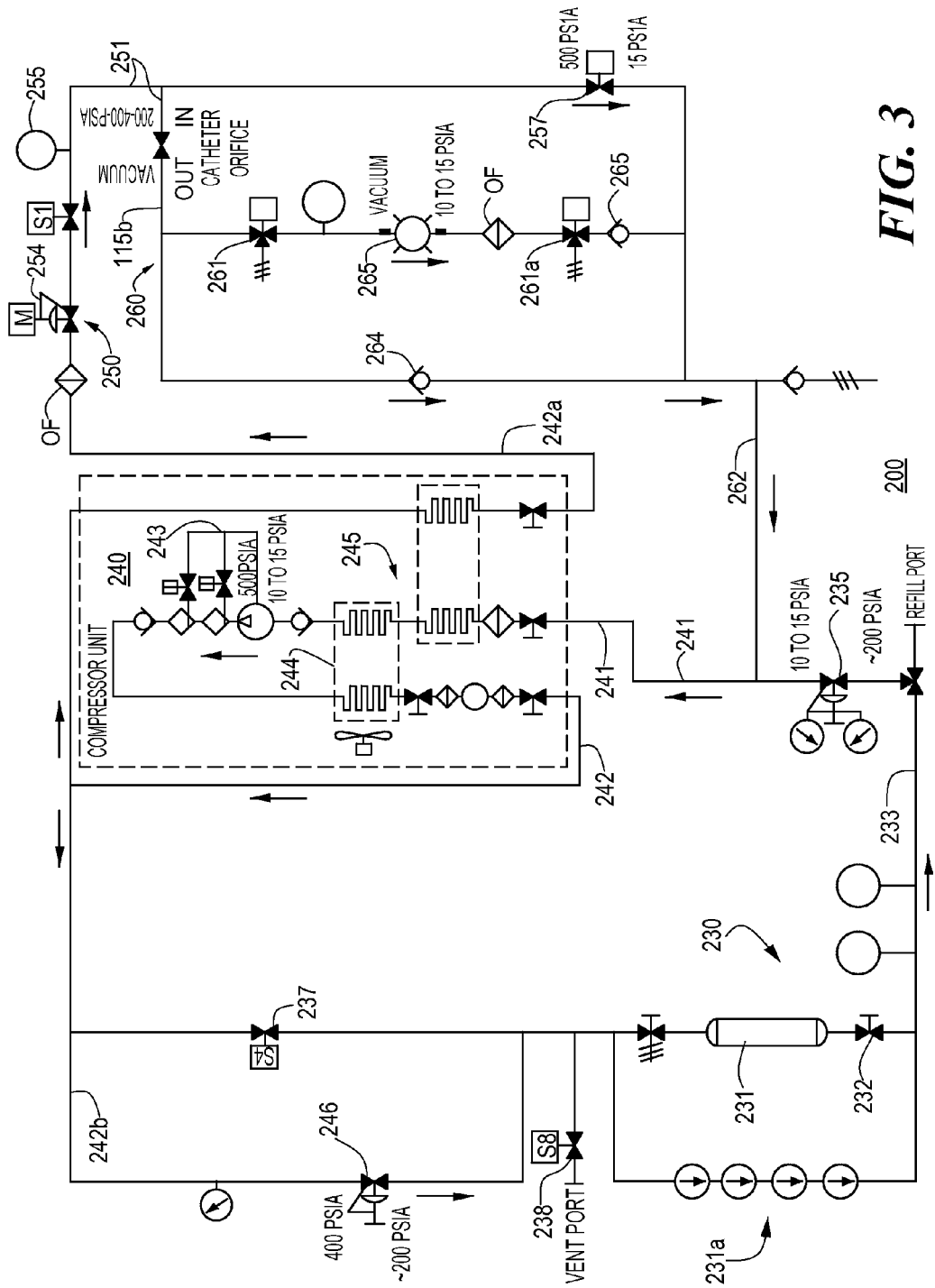
FIG. 3 is a detailed schematic of another implementation of the coolant system of the present invention.

FIG. 3 shows a prototype embodiment in greater detail, illustrating representative valves and regulators for implementing a preferred closed-loop coolant supply 200. The coolant supply, compressor, control and return portions of system 200 are numbered with numerals 230, 240, 250, and 260 corresponding to the related subassemblies 30, 40, 50 and 60 of system 20. As shown in this embodiment, a refrigerant tank 231 equipped with a magnetic sight glass 231a to indicate fill level, supplies refrigerant through a needle valve 232 along line 233 to a downstream pressure regulator 235. The pressure regulator 235 converts the nominal tank pressure of several hundred pounds per square inch to a fixed level of 14 psia to provide a constant supply pressure to the inlet line 241 of the compressor. At this stage the refrigerant is boiling at a temperature of about −60° Fahrenheit. The vacuum recovery return line 262 joins the refrigerant inlet 241 at this point.

The compressor inlet line 241 passes through heat exchanger 245 en route to the compressor 243, and also passes through a condenser 244, so the low pressure liquid in the inlet line 241 is heated by the hot vapor coming out of the compressor, causing it to become a vapor. The compressor 243 takes the vapor and pressurizes it to about 400 psi. The pressurized output passes along line 242 through dryers D and sight glass SG, after which the high pressure outlet line bifurcates into two branches 242b and 242a. An upstream pressure regulator 246 in line 242b builds and maintains pressure in the high pressure output line allowing the regulator to open and return excess refrigerant to the tank 231 when the pressure reaches a preset level, of about 400 psi, which is higher than the nominal tank pressure, e.g., 200 psi.

The second branch 242a of the output line 242 passes through the heat exchanger 245 located in the upstream portion of the input line 241, where it is further cooled to provide a conditioned output to the controller 250, which as shown includes a motorized pressure regulator 254. Pressure regulator 254 controls the flow rate of coolant provided along line 251 to the inlet port of the catheter (illustrated schematically). By way of example, the pressure regulator 254 may be controlled by a control microprocessor in the console to provide coolant at a pressure of 250 psi for a time interval of 2.5 minutes. Control is generally done by actuating the motor of regulator 254 to achieve a desired set point and leaving the regulator at that setting for the indicated time period. A zero to 500 psi pressure transducer 255 is placed in line 251 to provide feedback signals for implementing the control of the regulator 254, which may further employ feedback from the thermocouple in the catheter.

The foregoing values of pressure and duration are given by way of example only, and it will be understood that typical cooling regimens implemented by the control console 120 (FIG. 1) may run from several seconds to five minutes or more, and that the coolant pressures which are varied to achieve a desired rate of heat transfer or effective lesion depth may vary from the coolant pressure in the tank to approximately the pressure of the compressor output line 242*a*. Advantageously, the pressure in line 251 remains greater than the saturation pressure of the refrigerant being used such that it does not start to boil before it reaches the tip.

As further shown in FIG. 3, the return line 115*b* from the catheter attaches to vacuum section 260, while a solenoid operated purge valve 257 extends between the catheter inlet line 251 and the low pressure return line 262 from the vacuum scavenging system 260. It will be understood that purge valve 257 will typically be operated to bleed the inlet line when the catheter is first attached and the supply compressor or return pump, respectively, are operated.

The return line 115*b* from the catheter passes via vacuum protection solenoid-operated valve 261 to a vacuum pump 265, which maintains a vacuum in the range of 2 to 40 millibars in the return line, and which increases the pressure of the expended coolant vapor to approximately 15 psi. At the outlet side of the vacuum pump a similar solenoid operated protection valve 261*a* is provided together with a check ball, and an oil filter OF which prevents pump oil from contaminating the circulating coolant or depositing in the coolant valves, catheter passages or other components. A filter, e.g., 0.5 μm, appears in the catheter inlet line 251. The entire vacuum system may be isolated by the solenoid operated protection valves 261, 261*a*, during start-up or during a sensed overpressure or blood leakage condition, and a check valve 265 prevents any pressure build-up on the vacuum pressure side of the catheter in the event of pump or compressor failure, allowing coolant return directly into the return line 262 and compressor inlet 241; For this purpose, the compressor output or various bypass or check valves 257, 264 are set a pressure slightly higher than the output setting of the tank conditioner regulator 235, so that the coolant normally circulates into the catheter and through the vacuum system back into the compressor as a closed-loop.

In the illustrated embodiment, a coolant refill port 275 is provided at a solenoid operated valve 277 in the compressor inlet line 241, allowing a refrigerant bottle attached at that point to employ the same compressor 243 of the system to refill the supply tank 231. For this purpose, a solenoid operated by-pass valve 237 is also supplied to bypass the upstream high pressure return regulator 246 between the compressor output line 242*b* and the tank, and speed up refill of the tank 231. Preferably, above the tank, a solenoid operated valve 238 connects to a vent port to allow venting of any air which may have accumulated in the refrigerant tank due to leakage through the catheter or tubing. This vent is preferably controlled automatically by a suitable control program in the console 120. Venting may be implemented, for example, by providing a temperature sensor in the refrigerant tank and a pressure sensor at its top. Knowing the temperature of the liquid refrigerant in the tank, the vent may be operated until the saturated pressure is reached for the given refrigerant at the indicated tank temperature. Such a venting step is to be performed each time the console is turned on. In addition to the foregoing elements, various pressure indicators or temperature sensors may be situated along the different lines to indicate operating parameters of the fluid therein. These are preferably sensors or indicators of the process control type wherein, rather than a dial display output, they provide an electrical output which connects to a microprocessor programmed to monitor the various conditions continuously to detect relevant safety, control or maintenance conditions.

Figure 4A:
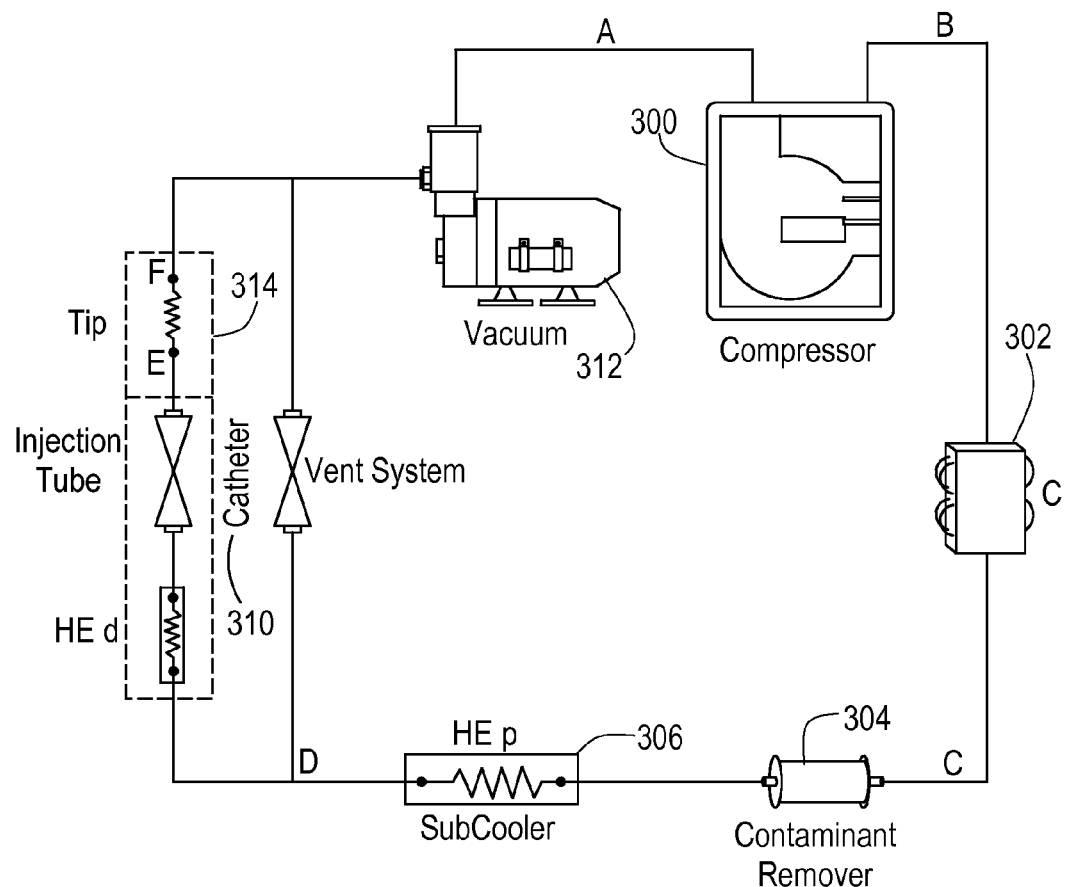
FIG. 4A is a schematic illustration of still another coolant system configuration.
Figure 4B:
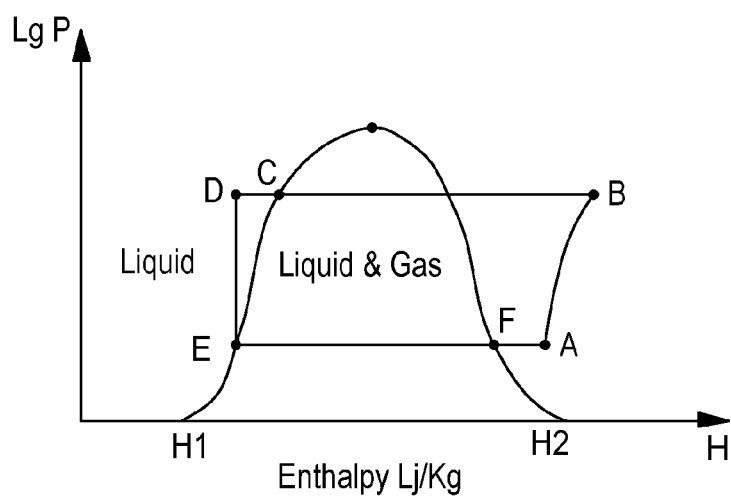
FIG. 4B is an enthalpy graph with respect to the system of FIG. 4A.

Referring now to FIG. 4A another embodiment of a closed-loop system is shown schematically, wherein letters A through F correspond to points on a system enthalpy graph depicted at FIG. 4B. Of particular interest in the graph of FIG. 4B are the areas representing a refrigerant in liquid state, gas state, and a mixed state that includes variable percentages of liquid and gas.

The system of FIG. 4A includes a compressor 300 that pressurizes refrigerant in a gas state and passes it through a first cooler or condenser 302. In the condenser 302, the refrigerant transitions from a gas state to a transition or combination liquid and gas state, wherein almost all of the refrigerant is liquid, or if liquid, very close to the point where the refrigerant changes state to a gas. The refrigerant passes through a filter or contaminant remover 304 and thence to a secondary cooler, referred to herein as a subcooler 306. The subcooler 306 chills the refrigerant to a lower temperature than that achieved by the compressor to cause the refrigerant to be completely in the liquid state prior to transfer to a catheter 310. In an exemplary system, the subcooler 306 chills the refrigerant to a temperature colder than 10° C. to enable the catheter tip to be chilled to temperatures as low as −90° C.

Ensuring that the refrigerant is in a liquid state before its introduction into the catheter provides significant performance advantages over known systems. For example, in order to achieved maximum cooling power and maintain a predictable and controlled tip temperature for a coolant injection system as described hereinabove, the refrigerant or coolant should exit the injection tube 1 (see FIG. 1A) as a liquid. However, without a subcooler, the coolant is at or near point "C" as shown in FIG. 4B (at the liquid/gas border). Thus, as it enters the catheter and begins to warm, bubbles form in the coolant and the coolant exits the injection tube 1 in spurts instead of as a stream. In some instances, without a subcooler, only 40% or so of the coolant exits the injection tube 1 as a liquid, as about 60% or so of the coolant has already changed state to a gas. Because, there is less fluid to change state to gas, the cooling power of the device is reduced. Further, the liquid/gas spurts cause significant temperature fluctuations that can adversely affect a selected cryotreatment. Both the reduced cooling power and the temperature fluctuation phenomena are increasingly pronounced and problematic the more the diameter of the catheter and injection tube are reduced.

As shown, the subcooler 306 is located within the console 120 or one of its accessories 115*c*. This helps to minimize weight and cost of a disposable handle and or catheter components, and it allows the catheter to be much smaller in diameter than a catheter having a secondary or subcooler in the handle or in the catheter. Additionally, locating the subcooler 306 in the console and/or its accessories minimizes the space occupied or required by cooling equipment within the catheter, thereby facilitating use of very small diameter catheters (e.g., 3Fr to 7Fr) for cryotreatments.

Continuing to refer to FIGS. 4A and 4B, as the refrigerant is ejected from the line leading from the subcooler 306, it is allowed to change phase from a liquid to a gas and to expand in a low pressure or near vacuum environment created by a vacuum pump 312 at the catheter tip 314. FIG. 4B illustrates the sudden transition from liquid to gas as represented by points "D" to "E" to "F" and to "A" on the enthalpy graph. The vacuum pump 312 causes the expanded gas to be returned to the compressor 300 so the cycle can be repeated.

Figure 5A:
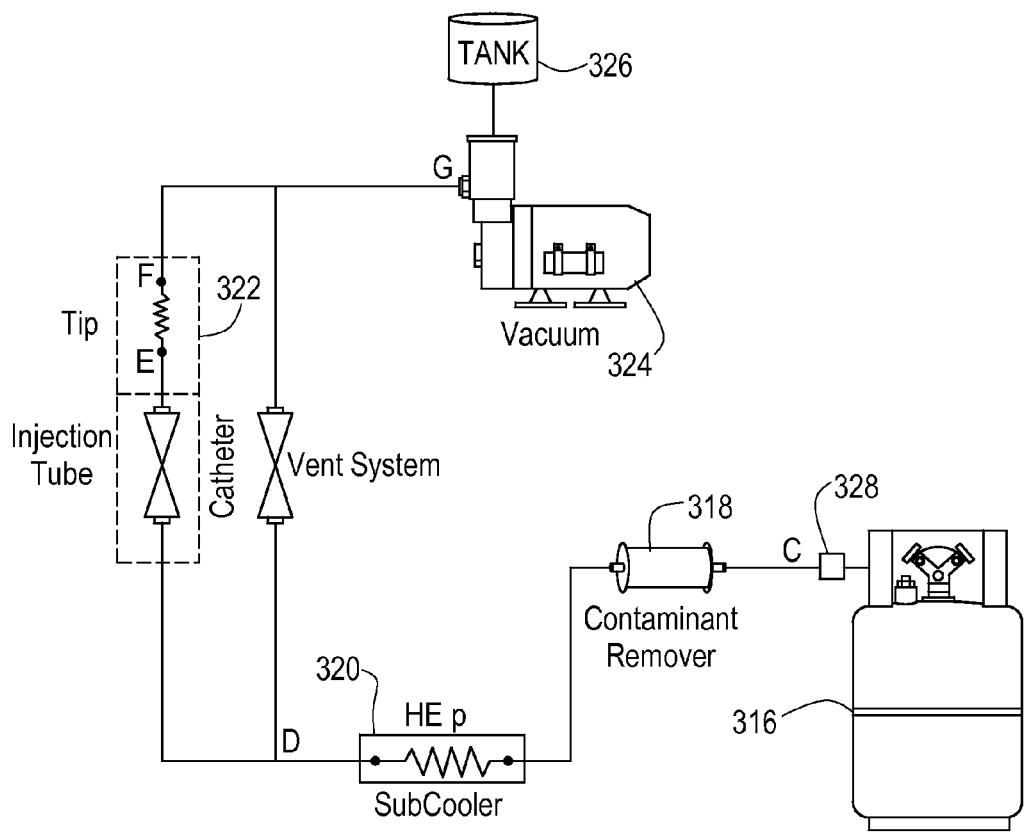
FIG. 5A is a schematic illustration of yet another coolant system Configuration.
Figure 5B:
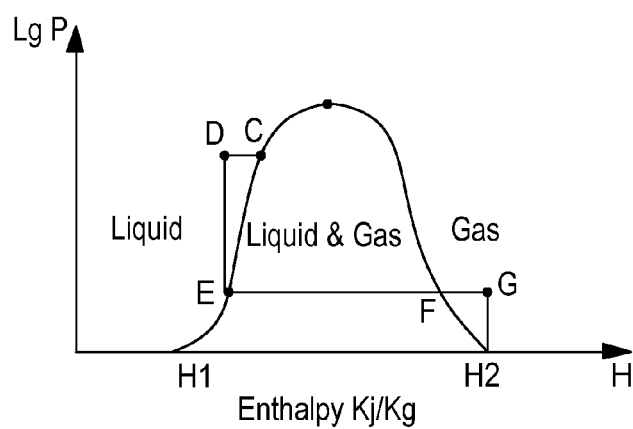
FIG. 5B is an enthalpy graph with respect to the system of FIG. 5A.

FIGS. 5A and 5B illustrate another cooling system configuration that is similar to the closed-loop system shown in FIG. 4A. In this embodiment, there is no compressor 300 or condenser 302. Refrigerant is supplied to the system from a tank or cartridge 316 in substantially liquid state or very close to the point where the refrigerant changes state from liquid to gas (point "C" on the graph of FIG. 5B). The refrigerant passes through a filter or contaminant remover 318 and then to a subcooler 320. The subcooler 320 chills the refrigerant to a temperature that causes the refrigerant to be completely in the liquid state (point "D" on the graph of FIG. 5B) prior to transfer to a catheter 322.

As the refrigerant is ejected from the line leading from the subcooler 320, it changes phase from a liquid to a gas and expands at the catheter tip 322 in a low pressure or near vacuum environment created by a vacuum pump 324. FIG. 5B illustrates the sudden transition from liquid to gas as represented by points "D" to "E" to "F" and to "G" on the enthalpy graph. The vacuum pump causes the expanded gas to conveyed to a collection tank or other scavenging system 326. Cryotreatment can continue until the refrigerant supply bottle 316 is no longer capable of providing liquid refrigerant. Down-time, however, can be minimized if a quick-connect/disconnect mechanism 328 is associated with the supply bottle 316. In an alternate configuration, a vacuum pump is not used and the expanded gas is directly conveyed to the collection tank or other scavenging system 326. In still another alternate configuration, the expanded gas is released to the atmosphere surrounding the system, with no scavenging or collecting system used. Various other configurations will be apparent to those skilled in the art based on the disclosures of the present invention.

Figure 5C:
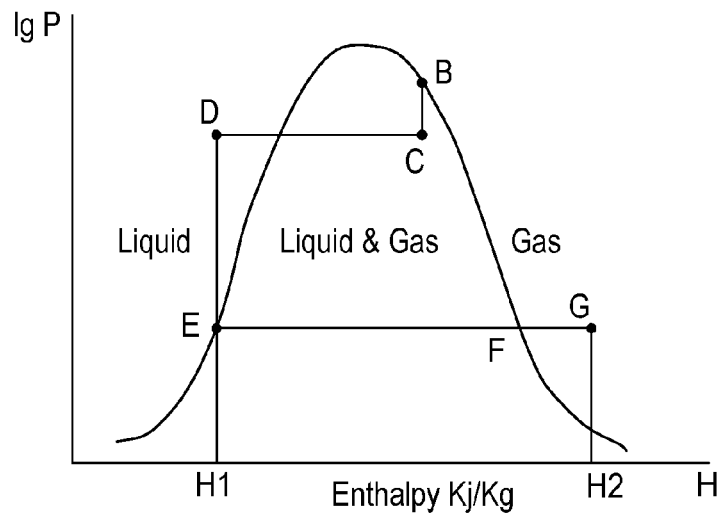
FIG. 5C is another enthalpy graph with respect to the system of FIG. 5A.

Referring now to FIGS. 5A and 5C, an alternate arrangement of a cooling system configuration is illustrated. Here refrigerant is supplied to the system from the tank or cartridge 316 in a substantially gas state (point "B" on the graph of FIG. 5C). The refrigerant passes through the filter or contaminant remover 318 (optional) and then to the subcooler 320. The subcooler 320 chills the refrigerant to a temperature that causes the refrigerant to transition to the liquid state (point "D" on the graph of FIG. 5C) prior to transfer to the catheter 322.

As the refrigerant is ejected from the line leading from the subcooler 320, it changes phase from a first liquid state to a second liquid state points "D" to "E") then to a gas and expands at the catheter tip 322 in a low pressure or near vacuum environment created by a vacuum pump 324. FIG. 5C illustrates the sudden transition from the second liquid state to the gas state as represented by points "E" to "F" and to "G" on the enthalpy graph. The vacuum pump causes the expanded gas to be conveyed to a collection tank or other scavenging system 326. Cryotreatment can continue until the refrigerant supply bottle 316 is no longer capable of providing liquid refrigerant. Again, down-time can be minimized if a quick-connect/disconnect mechanism 328 is associated with the supply bottle 316. It is contemplated that the phase states represented by FIG. 5C can be employed in any of the structural embodiments constructed in accordance with the present invention.

Supplying the refrigerant to the chamber 360 in a gas state has the added advantage of providing consistent control of the flow and temperature characteristics of the refrigerant. Refrigerant in the gas phase is less susceptible to fluctuations that can occur due to the refrigerant's inherently unstable nature at the gas-liquid transition phase.

Although a subcooler is shown with respect to the systems of FIGS. 4A and 5A, such a device can also be included in the systems depicted in FIGS. 2 and 3. A subcooler or subcooling system compatible with these systems can include a Peltier cooler, a Joule-Thompson, a Stirling engine or an independent closed-loop refrigeration system. Additionally, although control of the ratio of gas and liquid in a coolant can be performed with temperature control, the invention also contemplates use of pressure control in the console and subcooler to control the ratio.

Figure 6:
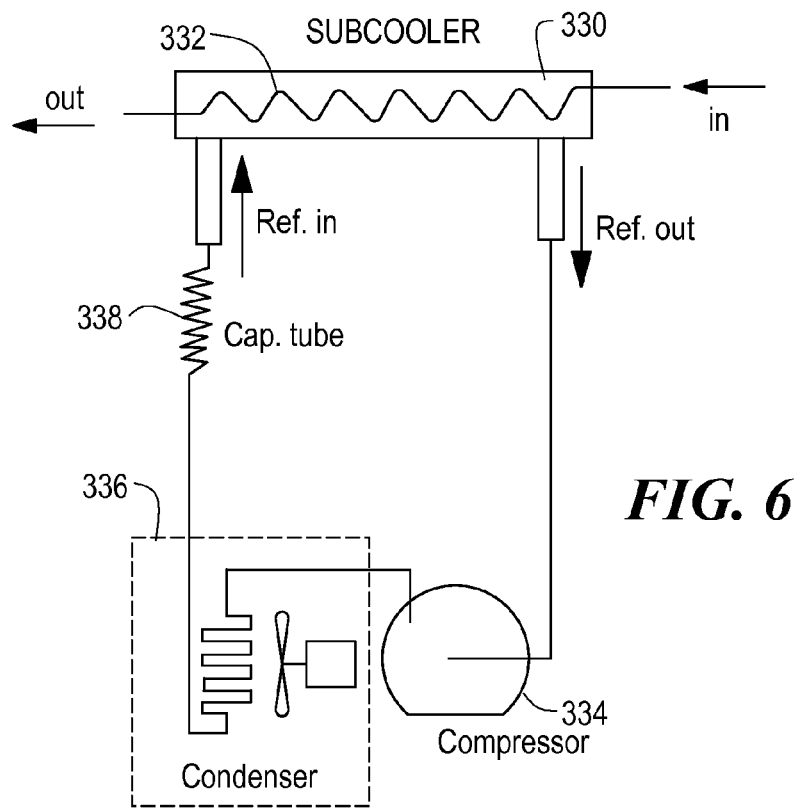
FIG. 6 schematically represents a refrigerant subcooler that can be included in the coolant system configurations of the invention.

FIG. 6 discloses an exemplary, independent, closed-loop subcooler in schematic form. As shown, the subcooler includes a chamber 330 through which passes a coiled refrigerant transfer line 332. A compressor 334 and condenser 336 provide liquid refrigerant that is transferred into the chamber 330 as shown by the arrow marked "Ref. in." The coolant, if compressed gas expands, or if liquid changes state to gas, thereby chilling the transfer line 332 and its contents. The expanded, gas-state coolant is exhausted from the chamber 330 as shown by the arrow marked "Ref. out" and returned to the compressor 334. A capillary tube 338 can be interposed between the condenser 336 and the chamber 330 in order to reduce the flow injected in the heat exchanger 330.

Although the subcooler system of FIG. 6, can provide effective cooling performance, it can also be bulky, noisy, and heat emitting when compared to the subcooling system of FIG. 7. Referring now to FIG. 7A, an insulated enclosure 340 (like chamber 330) encloses a coiled portion of a coolant supply line 342 leading to a medical implement (not shown) as described above. The coolant supply line 342 is in communication with a coolant reservoir 348 (such as bottled, liquid $N_2O$) to allow coolant to be directed into the enclosure 340. An outlet 350 in communication with a vacuum source 351 is provided to exhaust coolant from the enclosure 340 whereupon it is directed to a scavenging system. Cooling performance can be controlled with a coolant flow regulator 352 that can be made responsive to a temperature sensor 354 within the enclosure 340 that outputs a signal to a temperature controller 355 that controls the flow regulator 352. As discussed above coolant or refrigerant can be supplied in a liquid phase or a gas phase, for example, FIG. 7B is an enthalpy graph (representing refrigerant supplied in the liquid phase) for the system illustrated in FIG. 7A. Alternately, the enthalpy graph shown in FIG. 5C represents the phases of the coolant along the flow path (representing refrigerant supplied in the gas phase).

Figure 7A:
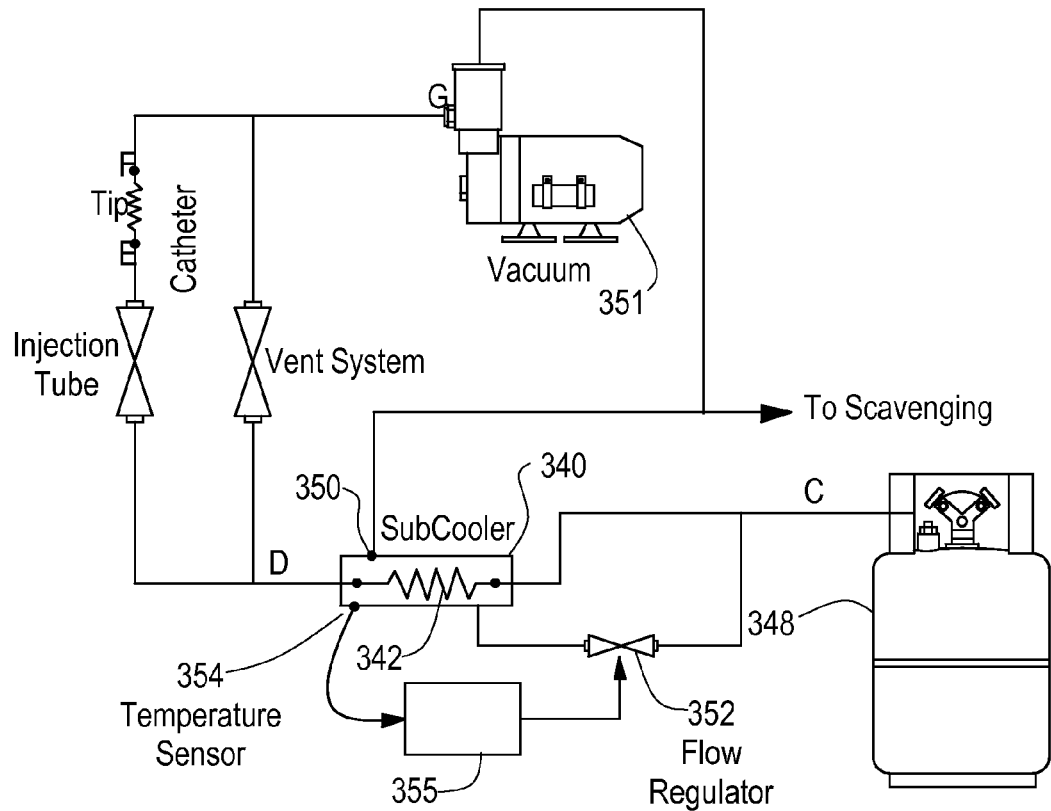
FIG. 7A illustrates another configuration for a subcooler.
Figure 7B:
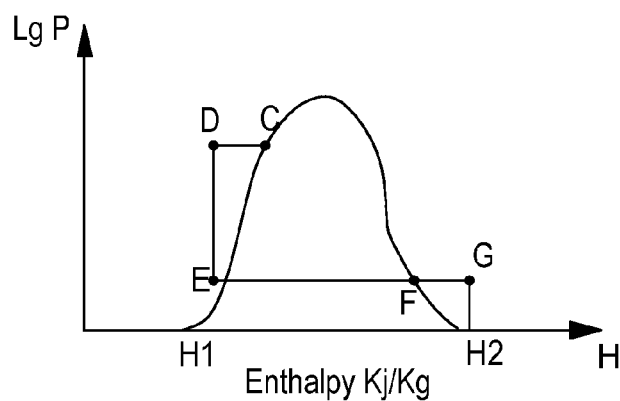
FIG. 7B is an enthalpy graph with respect to the system of FIG. 7A.
Figure 7C:
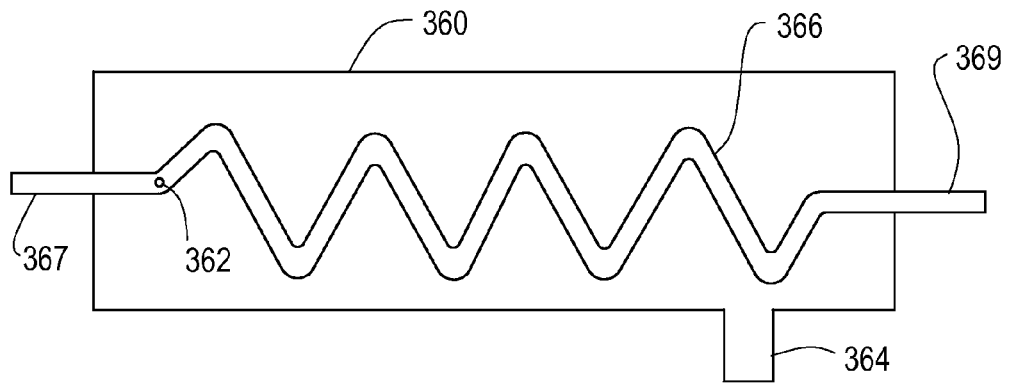
FIG. 7C is a schematic illustration of yet another coolant system configuration.

Referring now to FIG. 7C which is a schematic illustration of an alternate embodiment of a subcooler. Chamber 360 is depicted having an outlet 364. Provided within the camber 360 is a conduit 366, having a first end 367 and a second end 369, defining a fluid flow path for a coolant or a refrigerant. The conduit 366 defines an inlet 362. In practice, a refrigerant is supplied to the first end 367 which then passes through the body of the conduit 366 to the second end 369. After the refrigerant enters the conduit 366 a portion of the refrigerant is directed into the chamber 360 via the inlet 362, the refrigerant then expands to thereby cool the chamber 360 and in turn the conduit 366. The expanded refrigerant is then evacuated from the chamber 360 via the outlet 364. The rate of flow through the inlet 362 can be controlled by the size of the inlet 362 as well as by flow control valves as discussed herein (not shown). The diameter of the inlet 362 can range from 0.0001 to −0.03 inches. In an exemplary embodiment the diameter of the inlet 362 is 0.002 inches. The rate of subcooling affected within the chamber 360 can be regulated by adjusting the flow rate of the outlet 364. By decreasing the flow rate allowed at the outlet 364, the amount of refrigerant entering the chamber 360 via the inlet 362 is thereby decreased and the subcooling reduced. Further, it is contemplated that the location of the inlet 362 along the conduit 366 can be varied, for example, the inlet 362 can be provided closer to the second end 369 than is shown in FIG. 7C. It is also contemplated the that the location of the outlet 364 along the chamber 360 can be varied, for example the outlet 364 can be provided closer to the first end 367 than is shown in FIG. 7C. In an alternate configuration where a refrigerant is supplied to the subcooler in a liquid phase, it is advantageous to place the inlet 362 close to the first end 367 and the outlet 364 close to the second end 369. Alternatively, when the refrigerant is supplied to the subcooler in a gas phase, it is advantageous to provide the inlet 362 close to the second end 369 and the outlet 364 close to the first end 367. It is contemplated that the subcooler shown in FIG. 7C can be used in systems as shown in FIGS. 4A, 5A, 7A, 9 and 10 as well as other such systems.

Figure 7D:
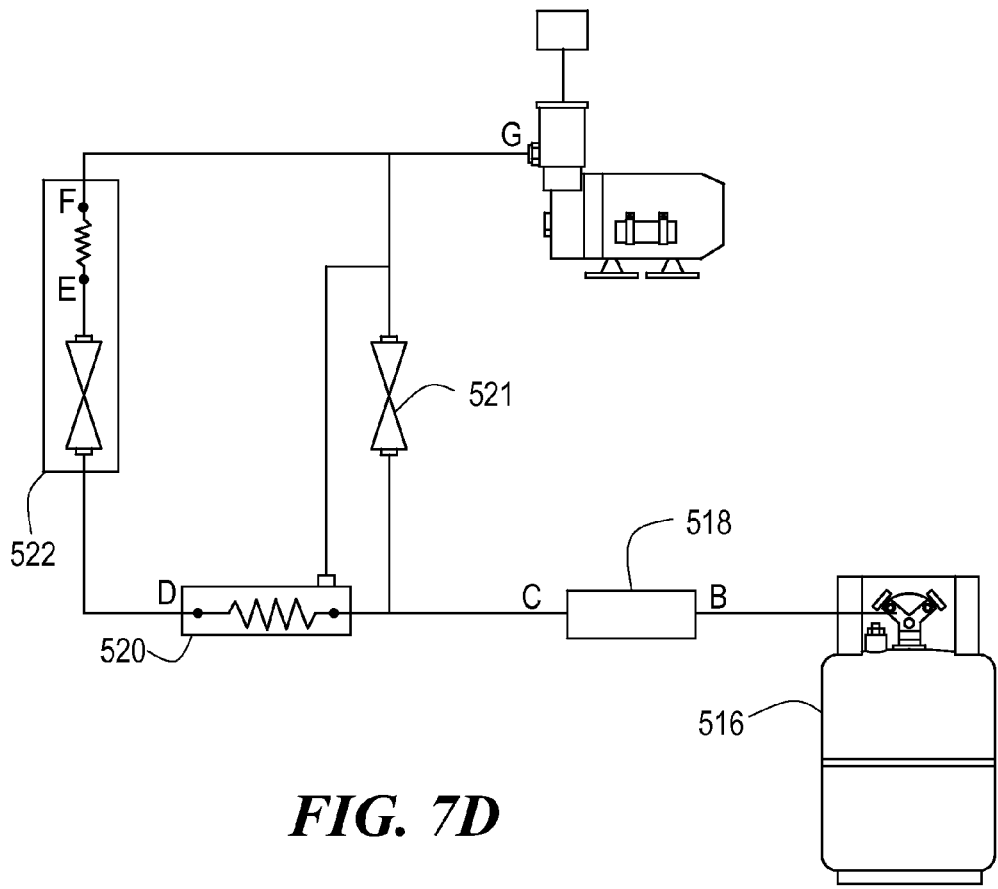
FIG. 7D is a schematic illustration of yet another coolant configuration.
Figure 10:
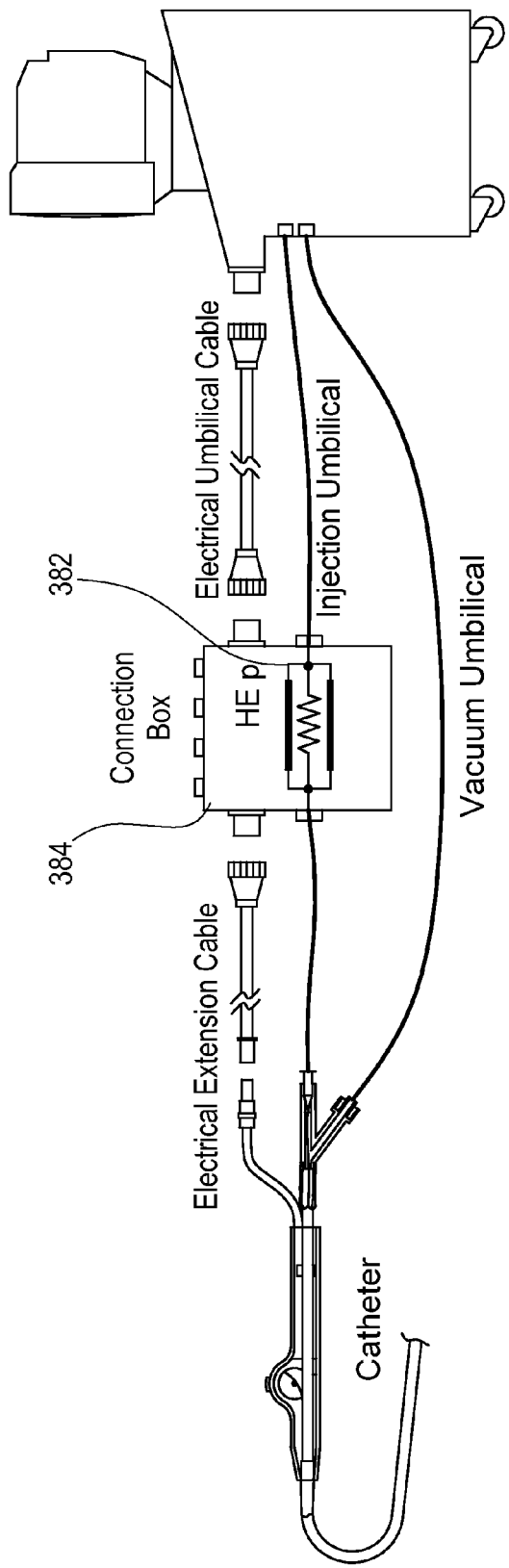
FIG. 10 is a schematic illustration of still another coolant system configuration.

Referring now to FIG. 7D which is a schematic view of another alternate embodiment of a subcooler illustrated in more detail. FIG. 7D illustrates another cooling system configuration that is similar to the closed-loop system shown in FIG. 5A with an alternate subcooler location and further incorporating the exemplary subcooler arrangement of FIG. 7C. Refrigerant is supplied to the system from a tank or cartridge 516 in substantially liquid state or substantially gas state as discussed in detail above. The refrigerant passes through a filter or contaminant remover 518 (optional) and then to a junction 519. One branch of the junction passes through a vent system 521 and the other branch passes through subcooler 520. The subcooler 520 chills the refrigerant to a temperature that causes the refrigerant to be in the liquid state prior to transfer to a catheter 522. The arrangement shown in FIG. 7D has the added advantage of permitting placement of the subcooler within accessories external to the console, for example, in an connection box as shown in FIG. 10 below, in a catheter handle assembly or any other such device located between the catheter and the console.

The function of the system shown in FIG. 7D follows that described above. It is contemplated that the subcooler embodiment shown in FIG. 7C can be used in any of the alternate systems discussed herein. It is further contemplated that the physical arrangement of the individual components can follow the layout shown in FIG. 7D as well as other arrangements disclosed herein.

Figure 8A:
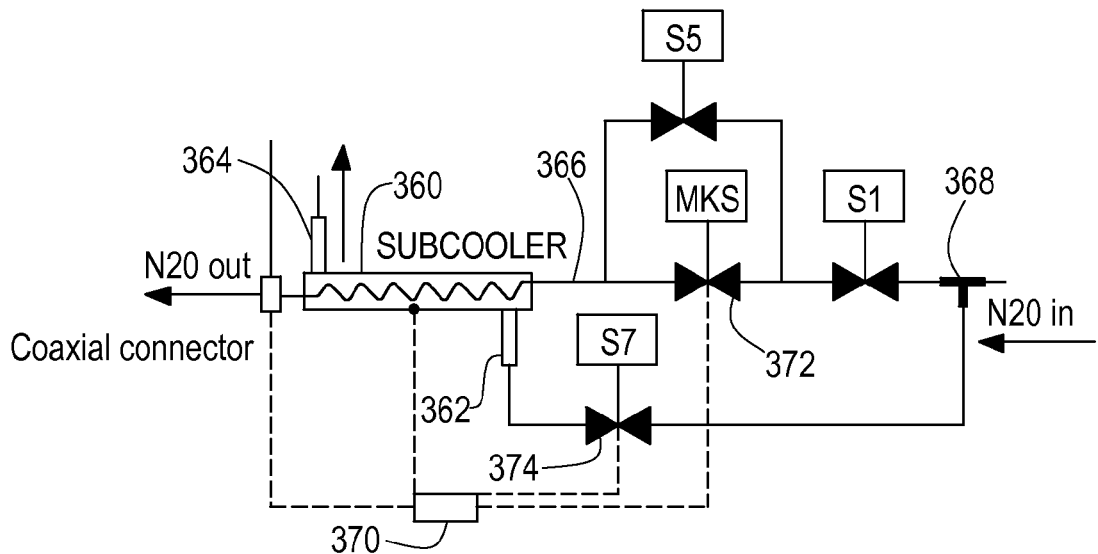
FIG. 8A illustrates still another configuration for a subcooler.

Referring now to FIG. 8A, yet another configuration for a subcooler is illustrated in conjunction with a control system for the subcooler. As with configurations described above, this illustration depicts a chamber 360, having an inlet 362 and an outlet 364, provides a flow path for refrigerant such as nitrous oxide or another fluid. A conduit 366 that defines a second fluid flow path for the same refrigerant passes through the chamber 360 and is in fluid communication with a refrigerant supply upstream of the chamber and a medical device downstream from the chamber. As shown, a fluid flow splitter 368 can allow a common refrigerant source to be used for supplying the chamber 360 and the conduit 366.

A programmable controller 370 is in communication with and controls one or more valves, such as a first valve 372, to regulate flow of coolant through the conduit 366 and into the medical device in response to a programmed cooling profile and in response to sensor outputs from the catheter. Additionally, the controller 370 can be used to control a second valve 374 to regulate flow of coolant through the chamber 360 in response to sensed temperature within the chamber. For example, the controller 370 can establish a duty cycle that opens and closes the second valve 374 repeatedly over time. If the temperature rises in the chamber 360 the second valve 374 can be opened and closed more frequently. By contrast, if the temperature in the chamber falls too far, the second valve 374 can be cycled less frequently. Another example includes establishing a duty cycle to specifically regulate the temperature increases and decreases at the treatment site. It has been found advantageous to be able to precisely control the freezing and thawing rates when performing a procedure as described above. Further, by sensing the actual temperatures and adjusting the opening and closing of the system valves, the application of specific temperature regimens can be accomplished.

Figure 8B:
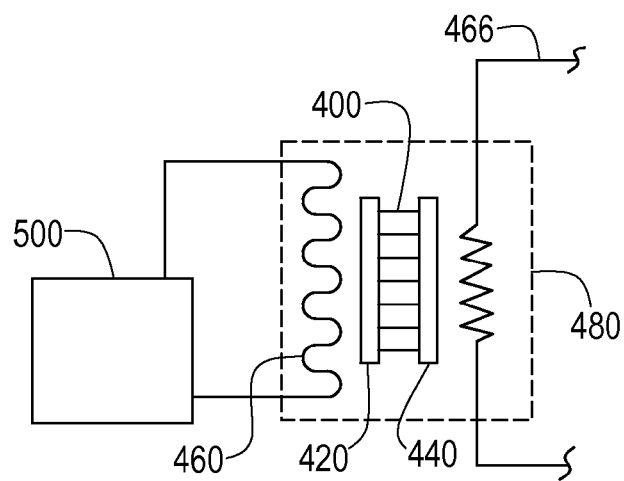
FIG. 8B illustrates still another configuration for a subcooler.

Referring now to FIG. 8B, yet another configuration for a subcooler is illustrated in conjunction with a control system for the subcooler. The subcooler feature is provided by a thermoelectric cooler 400, such as a peltier cooler, the operation of which is known in the art. The thermoelectric cooler has a hot side 420 and a cold side 440. A conduit 466 is provided adjacent and in thermally-conductive communication with the cold side 440 of the thermoelectric cooler 400. A supplemental cooler 460 is provided adjacent to and in thermally-conductive communication with the hot side 420 of the thermoelectric cooler 400. The conduit 466, the thermoelectric cooler 400 and the supplemental cooler 460 are enclosed by a housing 480. The supplemental cooler 460 is connected to an external cooling source 500 which can be any of the cooling arrangements disclosed herein or other such devices, for example, a compressor system as shown in FIG. 6 can be used.

Operation of the device shown in FIG. 8B is now discussed. When the thermoelectric cooler is activated, the temperature of the cold side 440 is reduced and thereby reduces the temperature of the adjacent conduit 466, which in turn reduces the temperature of refrigerant passing through the conduit 466. Further, the hot side 420 increases in temperature. The cooling source 500 supplies cold energy to the supplemental cooler 460 which thereby cools the adjacent hot side 420. By cooling the hot side 420, heat is removed from the housing 480 and the cooling efficiency of the supplemental cooler 460 is increased. As described above, it is desirable to provide a reduced temperature to the conduit 466 to thereby liquify any refrigerant or coolant that is passed through the conduit 466. It is further contemplated that the hot side 420 can be cooled by more conventional means such as moving air across the hot side 420. Additionally, a heat sink can be provided in thermal communication with the hot side 420 to increase cooling efficiency. Operations of such devices will be readily apparent to one skilled in the art based upon the disclosure of the present invention.

Figure 9A:
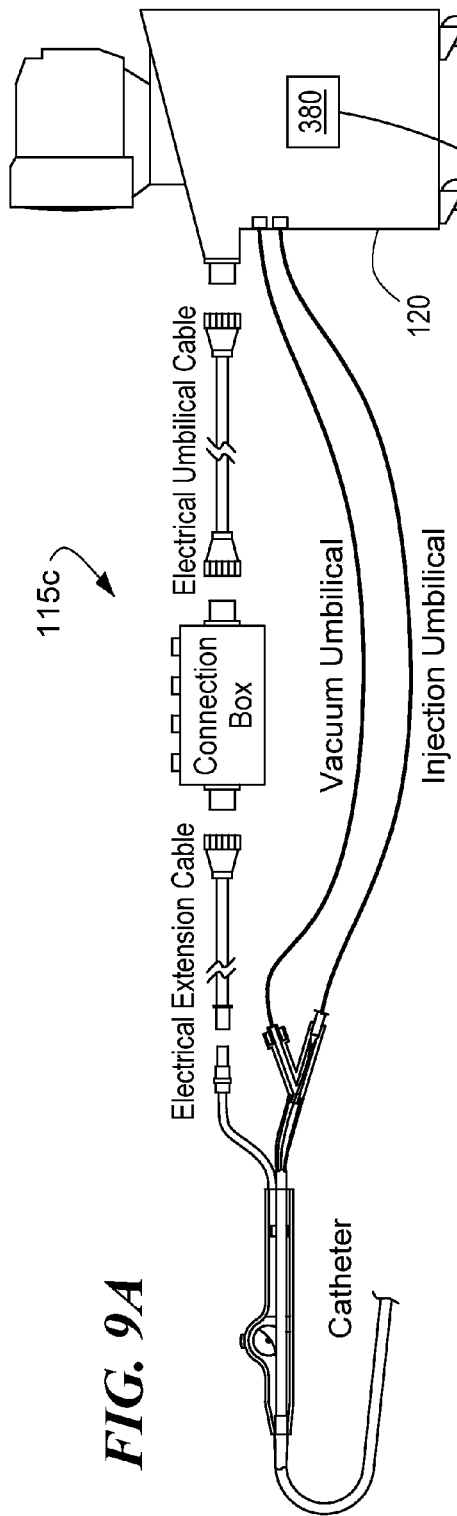
FIG. 9 is a schematic illustration of still another coolant system configuration.
Figure 9B:
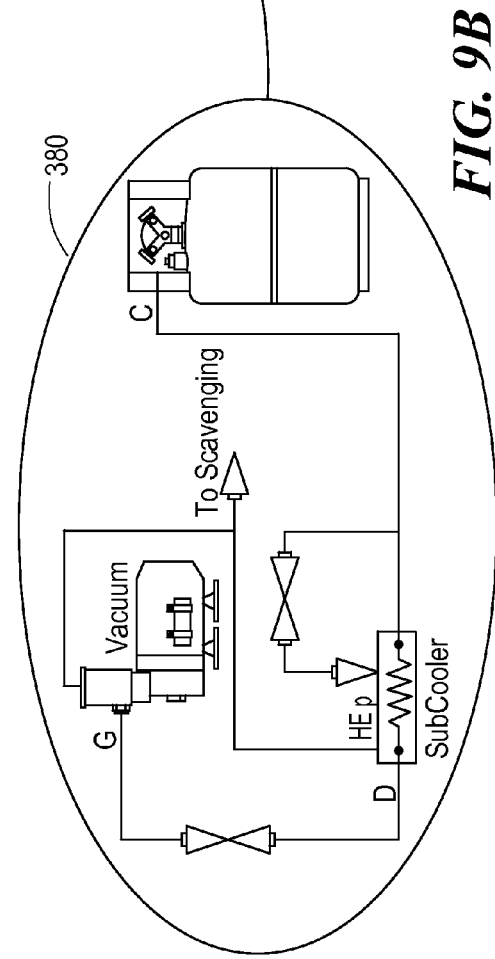

As discussed above, one significant advantage provided by the present invention is that subcooling systems can be located within the console 120 or its accessories 115c instead of in the catheter or in the catheter handle (the part held by the surgeon to manipulate the catheter). Thus, as used by applicant, "console" is intended to mean any component that is not a part of the operative implement. For example, in the systems shown, the "console." can be considered to be everything but the catheter and the handle. Illustrations of this feature are shown in FIGS. 9 and 10, wherein FIG. 9 illustrates exemplary subcooling system components 380 being located entirely within the console 120. FIG. 10 illustrates a system wherein a subcooler 382 is positioned within an ECG connection box 384. Although the subcooler 382 can be configured for cooling as described above, it can include any other known cooling device that can be located within an accessory such as an ECG connection box.

The invention being thus disclosed and described in illustrative embodiments herein, variations and modifications as well as adaptations of the invention to other systems will occur to those skilled in the art, and all such variations, modifications and adaptations are considered to lie within the scope of the invention as described herein and defined in the claims appended hereto and equivalents thereof.

What is claimed is:

1. A method of cooling a medical device, comprising:
providing a refrigerant in an unexpanded gaseous phase from a coolant source to a first pathway;
diverting a portion of the unexpanded refrigerant flowing through the first pathway into a second pathway at a first location, the second pathway returning at least a portion of the unexpanded refrigerant to the coolant source, the unexpanded refrigerant remaining in an unexpanded state throughout the entirety of the second pathway;
sub-cooling the undiverted expanded refrigerant in the first pathway to a temperature below a critical temperature thereof;
expanding the sub-cooled refrigerant in the medical device; and
directing at least a portion of the expanded refrigerant from the medical device to the first pathway upstream of the first location.

2. The method according to claim 1, wherein the coolant source is a pressurized tank.

3. The method according to claim 1, wherein providing the refrigerant includes pressurizing the coolant source with a compressor.

4. The method according to claim 1, wherein sub-cooling the undiverted unexpanded refrigerant in the first pathway includes directing the undiverted unexpanded refrigerant through a heat exchanger positioned such that a first segment of the first pathway is in a heat-exchange relationship with a second segment of the first pathway.

5. The method according to claim 1, wherein diverting a portion of the refrigerant flowing through first pathway into a second pathway includes providing a fluid flow splitter.

6. The method according to claim 1, wherein the refrigerant is sub-cooled to a temperature of less than approximately 10 degrees Celsius.

7. A cryogenic medical system, comprising:
a coolant source providing a refrigerant in an unexpanded gaseous phase to a first fluid pathway;
a catheter defining an expansion chamber therein, wherein the expansion chamber is in fluid communication with the first fluid pathway;
a flow splitter dividing a portion of the unexpanded refrigerant in the first fluid pathway into a second fluid pathway, the second fluid pathway returning unexpanded refrigerant to the coolant source and the unexpanded refrigerant remaining in an unexpanded state throughout the entirety of the second fluid pathway;
a subcooling system in thermal communication with a portion of the first fluid pathway; and
an exhaust pathway returning expanded coolant from the catheter to the first fluid pathway upstream of the flow splitter.

8. The cryogenic medical system according to claim 7, wherein the coolant source is a pressurized tank.

9. The cryogenic medical system according to claim 7, further comprising a flow regulator disposed within the first fluid pathway.

10. The cryogenic medical system according to claim 7, wherein the subcooling system includes a first heat exchanger positioned such that a first segment of the first fluid pathway is in a heat-exchange relationship with a second segment of the first fluid pathway.

11. The cryogenic medical system according to claim 10, wherein the subcooling system further includes a compressor coupled to the first fluid pathway between the first and second segments of the first fluid pathway.

12. The cryogenic medical system according to claim 11, wherein the subcooling system further includes a second heat exchanger positioned such that a third segment of the first fluid pathway upstream of the compressor is in a heat-exchange relationship with a fourth segment of the first fluid pathway downstream of the compressor and the flow splitter.

* * * * *